(12) United States Patent
Touati

(10) Patent No.: US 8,646,456 B2
(45) Date of Patent: Feb. 11, 2014

(54) ANTIBACTERIAL AGENT, AND DEVICE USED FOR ACTIVE PROTECTION OF INCISION MARGINS AND INCORPORATING SUCH AN ANTIBACTERIAL AGENT

(76) Inventor: Gilles Touati, Amiens (FR)

( * ) Notice: Subject to any disclaimer, the term of this patent is extended or adjusted under 35 U.S.C. 154(b) by 459 days.

(21) Appl. No.: 12/809,625

(22) PCT Filed: Sep. 30, 2008

(86) PCT No.: PCT/FR2008/051760
§ 371 (c)(1),
(2), (4) Date: Oct. 20, 2010

(87) PCT Pub. No.: WO2009/080922
PCT Pub. Date: Jul. 2, 2009

(65) Prior Publication Data
US 2011/0197897 A1    Aug. 18, 2011

(30) Foreign Application Priority Data

Dec. 20, 2007 (FR) ........................ 07 08933
Jan. 18, 2008 (FR) ........................ 08 50316

(51) Int. Cl.
*A61B 19/00* (2006.01)
(52) U.S. Cl.
USPC ................. 128/853; 602/42; 602/43; 602/48

(58) Field of Classification Search
USPC ........ 602/41–59; 424/443–449; 128/849–855
See application file for complete search history.

(56) References Cited

U.S. PATENT DOCUMENTS

| | | | |
|---|---|---|---|
| 2,858,830 A * | 11/1958 | Robins ........................ | 604/307 |
| 2004/0103903 A1 | 6/2004 | Falahee | |
| 2005/0249791 A1 | 11/2005 | Hobbs et al. | |
| 2006/0065275 A1 | 3/2006 | Lamprich | |

FOREIGN PATENT DOCUMENTS

| | | |
|---|---|---|
| FR | 0609220 | 10/2006 |
| WO | PCT/FR2007/052197 | 10/2007 |

OTHER PUBLICATIONS

International Search Report, Mar. 12, 2009, from International PHase of the instant application.

\* cited by examiner

*Primary Examiner* — Kim M Lewis
(74) *Attorney, Agent, or Firm* — Jackson Patent Law Office

(57) ABSTRACT

Antibacterial agents comprise as an active ingredient a hemostatic contact cloth having an acidic pH combined with povidone iodine. Also disclosed are surgical dressings. Also disclosed are devices for active protection of incision margins.

10 Claims, 6 Drawing Sheets

Figure 1A:
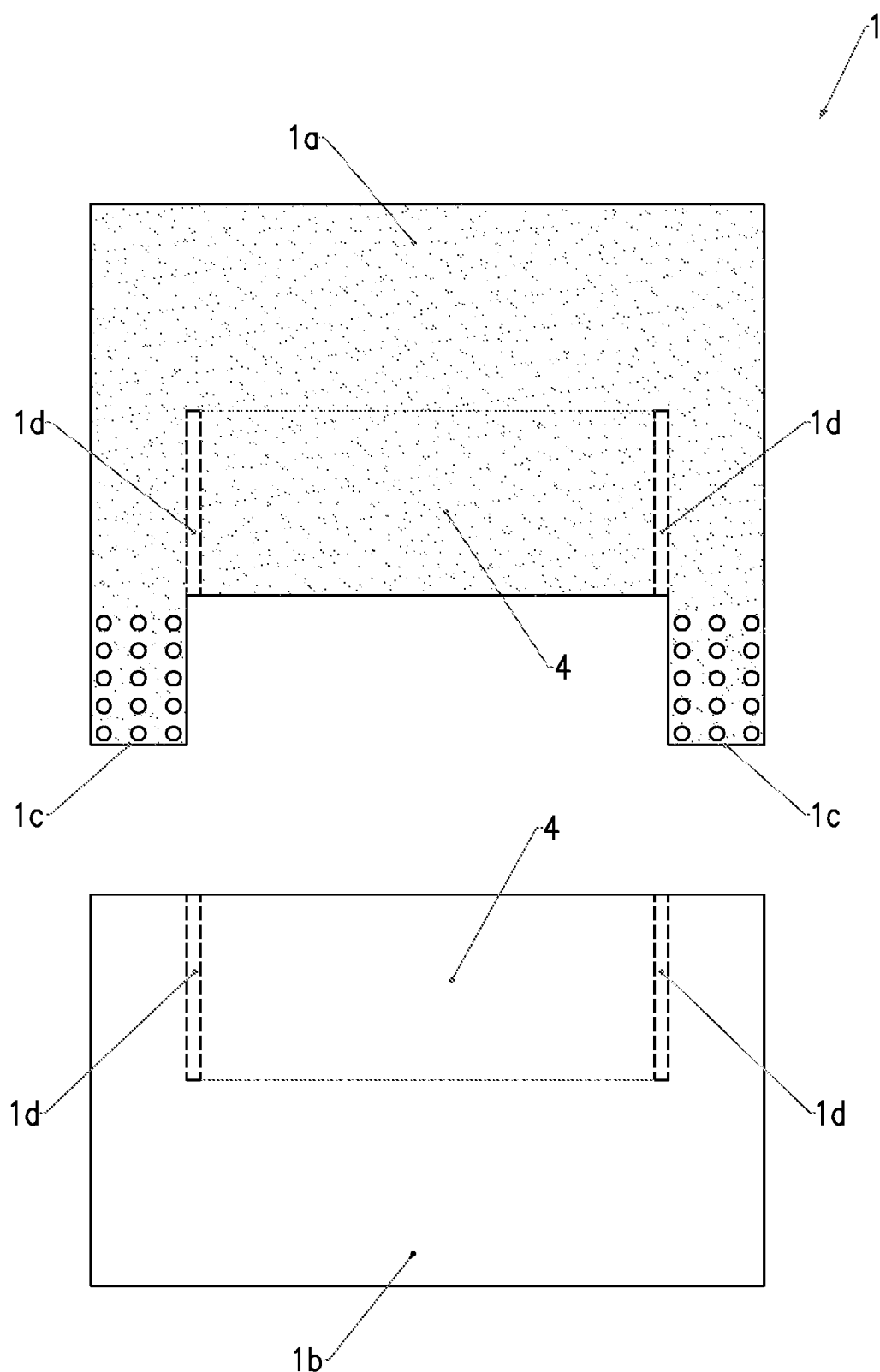

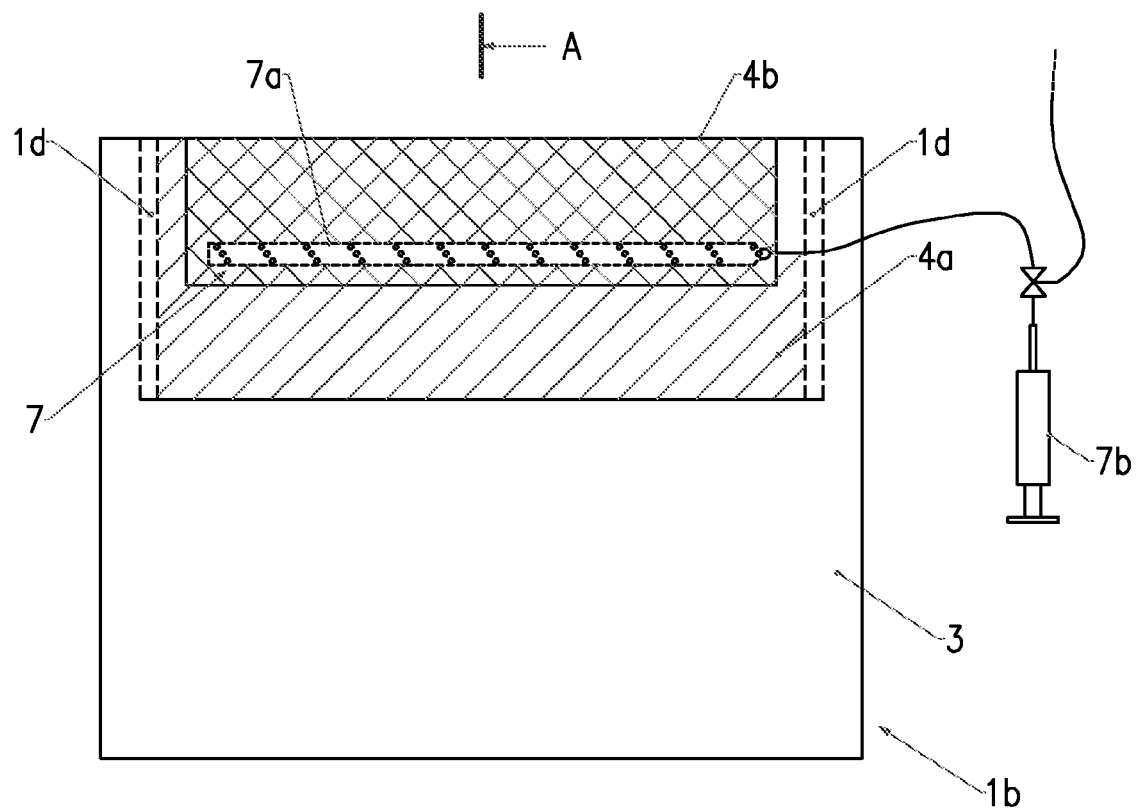
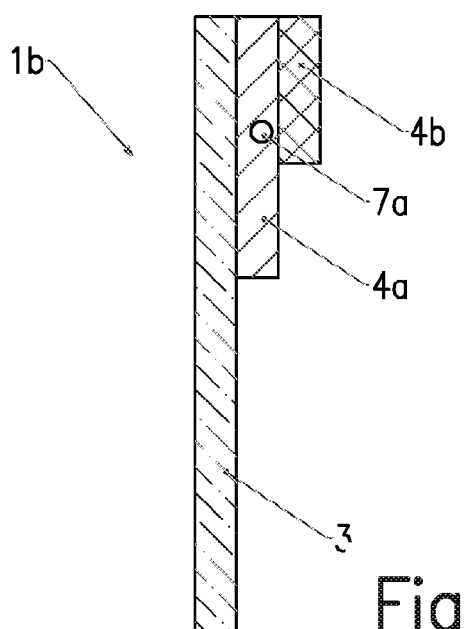

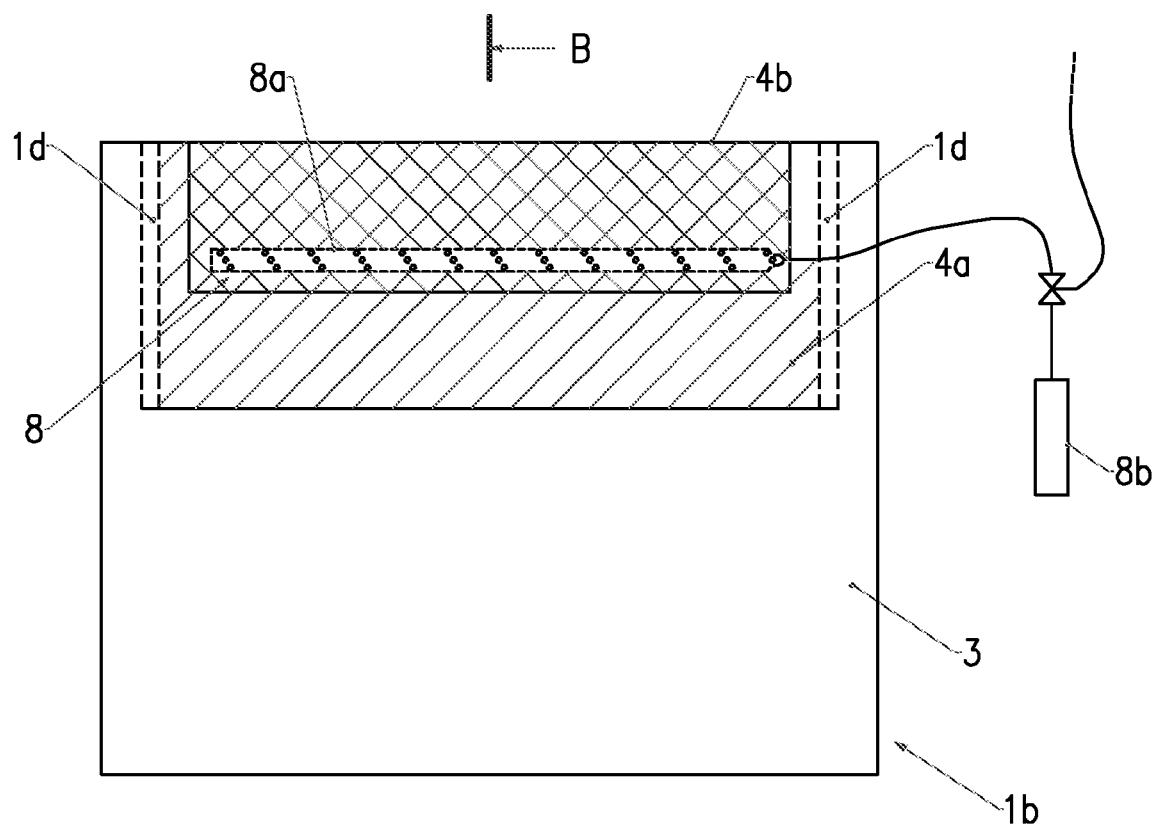
Fig. 5
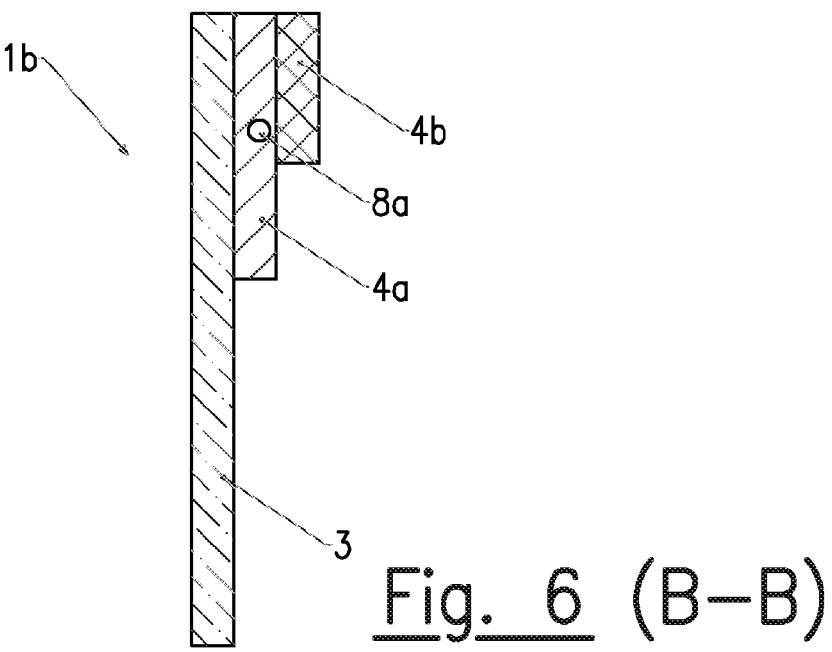
Fig. 6 (B-B)

ANTIBACTERIAL AGENT, AND DEVICE USED FOR ACTIVE PROTECTION OF INCISION MARGINS AND INCORPORATING SUCH AN ANTIBACTERIAL AGENT

TECHNICAL FIELD OF THE INVENTION

An object of the present invention is an antibacterial agent comprising as an active ingredient a hemostatic contact cloth having an acidic pH combined with povidone iodine. It also relates to an active protection device for incision margins incorporating such an antibacterial agent.

The invention relates to the technical filed of antibacterial agents designed to be used in humans and/or animals in order to protect and/or treat a wound and/or incision against bacterial infections. It also relates to the technical field of surgical accessories enabling protection of the incision margins during a surgical operation. The invention relates more particularly to the technical field of surgical drapes.

PRIOR ART

Hemostatic contact cloths are usually used for the treatment of hemorrhages, uncontrollable by conventional techniques, either cutaneous or internal (capillary and venous or arterial hemorrhages; oozing bleeding; cardiac and vascular surgery, neurosurgery; urology; . . . ).

By design, these hemostatic cloths typically have acidic pH so that they indirectly have an antibacterial activity. However, manufacturers recommend not using it for antibacterial purposes. In practice, the antibacterial activity must be carried out by an agent specifically designed for this purpose.

Povidone iodine (or polyvinylpyrrolidone iodine) is an external agent that liberates inorganic iodine acting directly on the cytoplasmic proteins to the state of free iodine. Povidone iodine is known for its antibacterial, antiseptic or antifungal properties. Although extremely effective, povidone iodine has a limited use because it does not enable treatment of all strains of germs that can cause antiseptic/antibiotic cross-resistances.

Known from the document SPALNGLER et al: "In Vitro Antimicrobial Activity of Oxidized Regenerated Cellulose Against Antibiotic-Resistant Micro-Organisms" SURGICAL INFECTIONS, vol. 4, No. 3, 2003, pages 255-262, is the result of an in-vitro study regarding the antimicrobial activity of oxidized regenerated cellulose materials. This study demonstrates the effectiveness of oxidized regenerated cellulose on micro-organisms resistant to multiple antibiotics, and more particularly the importance of an acidic pH. This study does not however make mention of the antimicrobial combination between the oxidized regenerated cellulose and povidone iodine.

A first technical problem the invention aims to resolve is to offer a new agent having an antibacterial activity superior to that of a hemostatic cloth and superior to that of povidone iodine, in order to be capable of treating a wide range of strains of germs and in particular certain germs resistant to antibiotics.

Also, during surgical operations, it is common to use surgical drapes provided with incision windows through which surgical procedures are performed. These drapes are placed on the skin of the patient and have the purpose or isolating and protecting the incision area against any contamination. They form an effective barrier between the body of the patient and the atmosphere of the operating room.

The surgical drapes usually used are made from a supple nonwoven sterile material. Generally, the lower surface in contact with the skin of the patient is adapted to absorb body secretions such as bleeding, while the upper surface is impermeable to the fluids. It is common to use cutaneous drapes iodized or impregnated with an antimicrobial substance, having a residual effect on the microbes present on the skin of the patient (mainly cutaneous staphylococci). Such drapes are for example described in WO 2005/110082 (3M), WO 00/71183 (3M), EP 0,812,893 (MEDICAL CONCEPTS DEVELOPMENT), EP 0,240,097 (SURGIKOS), EP 0,136,900 (SURGIKOS) or FR 2,012,584 (T. J. SMITH et al). These drapes can be adhesive to remain perfectly in place throughout the operation and at the border closest to the incision area.

Although widely used, these surgical drapes are not fully effective insofar as since they are only cutaneous and do not protect the incision margins. Indeed, when the skin is cut, bleeding, even minimal, of these tissues and prolonged exposure to air cause these incision margins to present a risk of seeing infections develop, abscesses or bruises, quite harmful for the health of the patient.

To attempt to resolve this technical problem, the use of a flexible retractable tubular element that is positioned around the incision margins is known from the document WO 99/03416 (MEDICAL CREATIVE TECHNOLOGIES). This tubular element is nevertheless difficult to install by the practitioner, because its manipulation is complex. In addition, it is necessary to allow for tubular elements of different diameters so as to able to adapt to the size of the incision made, which is inconvenient and costly.

The document U.S. Pat. No. 4,089,331 (THE KENDALL COMPANY) also attempts to offer a solution by proposing to use a sterile compress added on the end of a surgical sheet along the edge of the incision window. This compress is arranged to be in a storage position prior to the incision—packed away in a specific pocket or folded up on top of the sheet—and in a position covering the incision margins after the incision. The design of this device appears to be particularly complex because there a need for a storage pocket or a device enabling maintenance of the compress in folded position. In addition, the length of the compress cannot be easily adjusted so that the aforementioned compress can interfere with the operation of the practitioner when it is not adapted to the depth of the incision. Also, this compress is not particularly effective against infection or against the formation of abscess or hematoma.

The document GB 2,221,620 (Johnson & Johnson) discloses a dressing comprising a fibrous substrate whose surface is coated with a pharmacologically acceptable alginate. This type of dressing is not, however, specifically adapted to protect the incision margins and prevent development of infections during a surgical operation.

The existing surgical drapes are not completely effective insofar as they do not enable effective cleaning of the surgical site. Indeed, when the skin is cut, incision secretions appear (bleeding and/or bodily secretions) that are liable to damage the incision margins and cause infections of the wall and/or surgical site, particularly nosocomial infections. In addition, these secretions obscure parts of the operating site and thus hamper the smooth running of the surgical operation. It is therefore necessary to evacuate secretions of incision, generally by using absorbent compress that are changed regularly once they are completely infused. The absorption of secretions by compresses leads to additional maneuvers around the operating site, liable to interfere with the practitioner's execution of surgical procedures.

The sterile compress, added to the end of the surgical sheet described in U.S. Pat. No. 4,089,331 cited earlier, does not enable efficient absorption of the secretions of incision.

Indeed, once the compress is fully infused, the absorption of secretions can no longer be carried out so that one must continue to use additional absorbent compress and, therefore, continue to perform the additional maneuvers around the surgical site.

Known from the document WO2003/018098 (KCI LICENSING INC.) is a system designed to stimulate the healing of a difficult to heal tissue. This system comprises a porous pad introduced into a wound as well as an airtight dressing secured over the pad, hence the achievement of a hermetic seal over the wound. A proximal end of a conduit can be connected to the dressing, a distal end of this conduit being connectable to a negative pressure source, such as an electric pump housed in a portable housing, or a vacuum wall outlet. A collector installed on the conduit enables the retention of the exudates aspirated from the wound during the application of a negative pressure. Although effective, this system is complex and completely covers the wound so that the practitioner has no access to the incision site. In addition, the system described in document WO2003/018098 (KCI LICENSING INC.) does not protect against possible wound nosocomial infections.

Given the disadvantages of the prior art and in particular those of the device described in U.S. Pat. No. 4,089,331 (THE KENDALL COMPANY), the second technical problem that the invention aims to resolve is to efficiently, rapidly and continually protect the incision margins without the practitioner having to perform complex maneuvers.

A third technical problem that the invention aims to resolve is to offer a device of the type described in U.S. Pat. No. 4,089,331 (THE KENDALL COMPANY) capable of protecting the incision margins regularly throughout the operation.

A fourth technical problem that the invention aims to resolve is to offer a device of the type described in U.S. Pat. No. 4,089,331 (THE KENDALL COMPANY) capable of cleaning effectively, regularly, and without the interference for the practitioner, the incision margins as well as the operating site throughout the surgical operation.

Yet another object of the invention is to offer a device for protecting incision margins enabling prevention of infections of the wall and/or operating site, and particularly preventing nosocomial infections.

DISCLOSURE OF THE INVENTION

Referring to the first technical problem, the applicant has now demonstrated surprisingly that the combination of oxidized regenerated or non-regenerated cellulose with povidone iodine was providing a bacterial inhibition superior to the simple use of oxidized regenerated or non-regenerated cellulose alone or of povidone iodine alone. It is therefore a synergistic effect that leads to the formation of a new both very powerful antibacterial and hemostatic agent.

The solution offered by the invention to resolve the second technical problem is a device for active protection of incision margins, designed to prevent development of infections, comprising a surgical drape wherein a total or partial incision window is arranged, and wherein:

the internal face of the borders of the incision window is covered by a first layer of a material designed to absorb the secretions from the incision and a second layer impregnated with an antiseptic hemostatic ingredient having the purpose of preventing the development of infections, the second layer partially covers the first layer, the aforementioned first layer being wider than the aforementioned second layer, the second layer is arranged so that it can come into contact with incision margins and cover the top part and the bottom part of the incision when installing a spacer, the second layer is an oxidized regenerated or non-generated cellulose cloth combined with povidone iodine.

These technical features enable the practitioner to directly position the borders of the incision window at the incision margins to effectively protect the latter.

The third technical problem is resolved when the second layer is coupled to an element enabling impregnation, on demand, of the hemostatic contact cloth with povidone iodine. Indeed, the practitioner thus has the opportunity to re-impregnate the hemostatic cloth with povidone iodine, when the quantity of the latter decreases during the course of the operation.

The solution offered by the invention to resolve the fourth technical problem is a device for active protection of incision margins, comprising a surgical drape wherein a total or partial incision window is arranged, the borders of the aforementioned incision window being arranged so that they can come into contact with the incision margins. In accordance with the invention, the internal face of the edges of the aforementioned incision window is covered by a layer of the material designed to absorb the secretions from the incision, the aforementioned layer being coupled to a tubing connected to a member enabling aspiration of the aforementioned absorbed secretions.

These technical features enable not only draining of the incision margin, but also to simply and regularly evacuate the secretions from the surgical site. The applicant also was also able to note that such a device was enabling effective prevention of infections of the wall and/or operating site, and particularly nosocomial infections.

PRESENTATION OF THE DRAWINGS

Figure 1B:
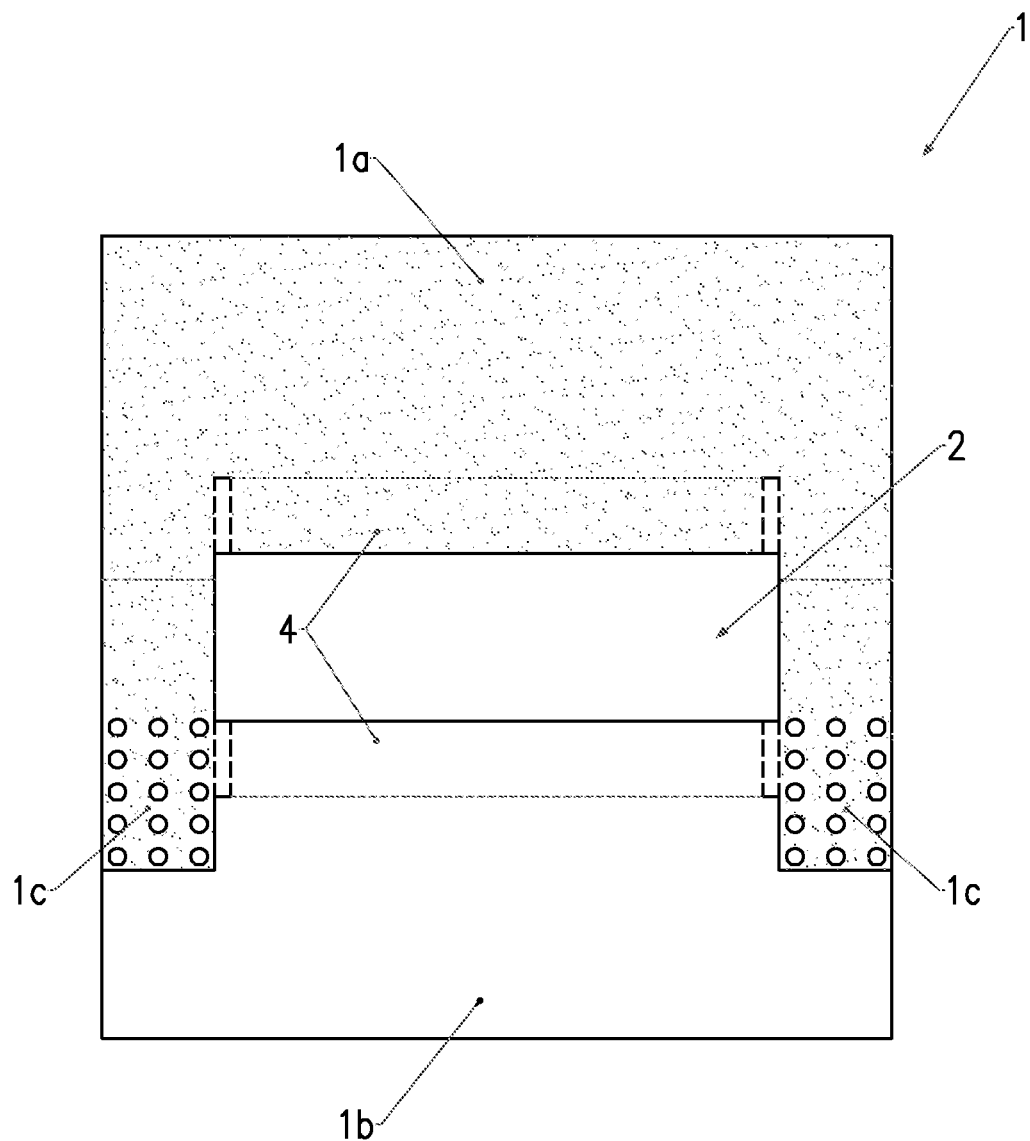
Figure 4:
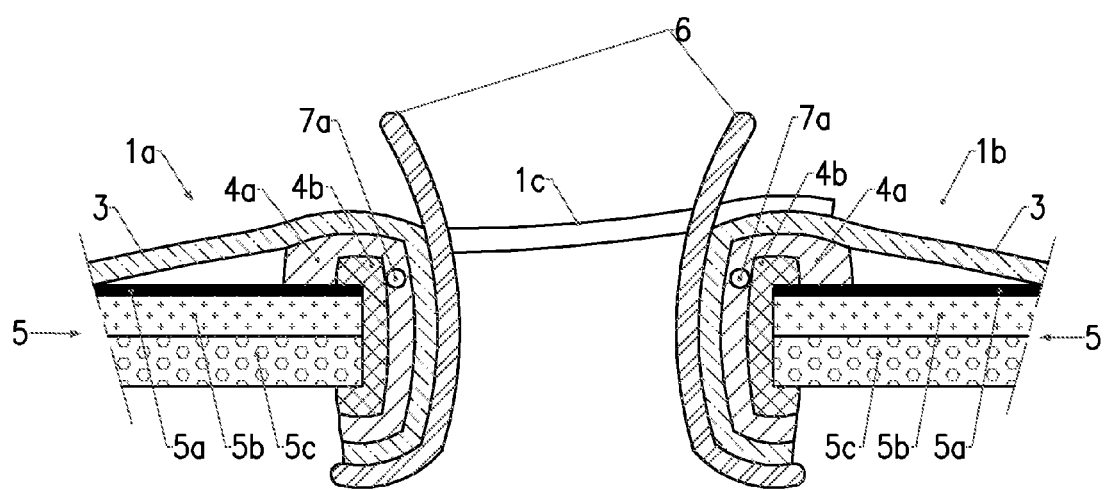
Figure 7:
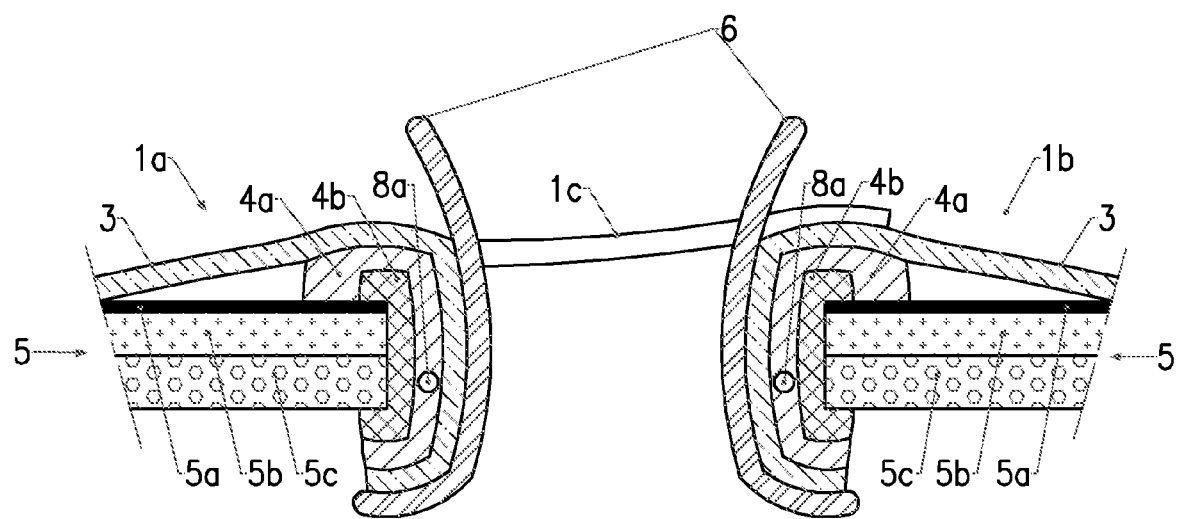

Other advantages and features of the invention will become more apparent upon reading the description of a preferred implementation mode that will follow, with reference to the accompanying drawings, made by way of indicative and not limiting examples and in which:

FIG. 1a is a schematic view showing the various constituent elements of the surgical drape in accordance with the invention, FIG. 1b is a schematic view showing the various constituent elements of FIG. 1a arranged so as to form the surgical drape in accordance the invention, FIG. 2 is a schematic view showing, full surface, the arrangement of the various constituent elements of the female part of the surgical drape in accordance with the invention, FIG. 3 is a sectional view along A-A of the female part of the surgical drape shown in FIG. 2, FIG. 4 is a schematic view showing, in section, the protection device of the invention positioned against the incision margins, FIG. 5 is a schematic view showing, full surface, the female part of the surgical drape provided with aspiration elements for the incision secretions, FIG. 6 is a sectional view along B-B of the female part of the surgical drape shown in FIG. 5, FIG. 7 is a schematic showing a view showing, in section, the protective device of the invention positioned against the incision margins and provided with aspiration elements for the incision secretions.

IMPLEMENTATION MODES OF THE INVENTION

In accordance with the invention, the antibacterial agent is characterized by the fact that it comprises as an active ingredient a hemostatic contact cloth having an acidic pH combined with povidone iodine.

This antibacterial agent is designed to be used in humans and/or animals in order to protect and/or treat wounds and/or incisions against bacterial infections. The use of the antibacterial agent is carried out by local application on the wound and/or the incision margins. For example, a surgical dressing incorporating the antibacterial agent in accordance with the invention can be used.

The posology will be adapted depending on the pH of the hemostatic contact cloth, the possible bacterial infection to be treated and the profile of the patient. To have a maximum effectiveness, the antibacterial agent optimally comprises between 70 μL and 130 μL of povidone iodine, pure or diluted, per 2 $cm^2$ to 16 $cm^2$ of hemostatic contact cloth. However, these dosages are not limiting and can be varied according to the needs of the person of skill in the art and according to the concentration of povidone iodine (0.1%, 1%, 10%, ...).

Oxidized regenerated or non-regenerated cellulose from wood pulp, cotton linters, cotton, ramie, jute, paper or similar materials, and also regenerated cellulose is preferably used as hemostatic contact cloth. For example, products known under the name: Surgicel®, Curacel®, Gelitacel®, OKCEL®, Resorcel®, Promogran®, etc. can be used.

The oxidized regenerated or non-regenerated cellulose is a resorptive contact hemostatic on the application site whose principal action is mechanical. The oxidized regenerated cellulose is a polymer and more particularly a polysaccharide composed of D-glucose molecules. The oxidation by the nitrogen tetroxide results in the oxidation of a part of the primary alcohol functions of the glucose with formation of glucuronic acid. The product obtained is a polymer of D-glucose and glucuronic acid.

As an example, the oxidation of the oxidized regenerated cellulose for making Surgicel® is carried out as follows: the oxidation is obtained by reaction of nitrogen tetroxide solution in the perfluorohexane. The coils are then washed with 50% Isopropyl alcohol until the achievement of a rinse effluent having PH>3.1. The coils are then rinsed twice in 99% isopropyl alcohol, then dried and packaged. The drying allows the elimination of the isopropanol. The gases are stored in a ventilated cabinet in a controlled atmosphere obtained by a succession of rises in temperature accompanied by partial vacuum operations. The residual isopropanol content is <5 ppm. The dehumidification phase leads to the almost total elimination of isopropanol. The oxidized non-regenerated cellulose can come from the oxidation of plant fibers and in particular from cotton (Gelitacel®, Okcel®,).

In an implementation variation, the hemostatic contact cloth is oxidized regenerated or non-regenerated cellulose impregnated with chitosan. The latter is a polymer derived from chitin, present in shellfish and certain plants and fungi. For example, products known under the name of: Chitoflex®, Chitoskin®, BST-Demon®, etc. can be used.

For the povidone iodine, products known under the name: Betadine®, Betaseptic®, Polydine®, Isocline®, Pevidine®, E-Z Scrub®, etc. can be used, for example.

In order to highlight the synergistic effect obtained by the combination of the hemostatic contact cloth having an acidic pH with povidone iodine, tests were carried out. These tests enable evaluation, on different bacterial strains, of:

the antibacterial power of a hemostatic contact cloth having an acidic pH alone, the antibacterial power of povidone iodine alone, the antibacterial power of hemostatic contact cloth having an acidic pH combined with povidone iodine.

Methodology:

According to the methodology of the NF EN ISO 20645 (August 2005) standard.

Equipment used:

Hemostatic contact cloth having an acidic pH:

oxidized regenerated cellulose (ORC) cloth made by the ETHICON® company (SURGICEL®). 2 cm×2 cm in double thickness, oxidized non-regenerated cellulose (ONRC) cloth made by the GELITA MEDICAL company (GELITACEL®). 2 cm×2 cm in double thickness, Povidone iodine: 10% Dermal Betadine®. Deposit of 93 μL on the cloth samples.

Bacterial strains:

| | |
|---|---|
| *Pseudomonas aeruginosa* | CIP 103 467 |
| Methicillin Resistant *Staphylococcus aureus* | CIP 103 811 |
| *Staphylococcus aureus* | CIP 4.83 |
| *Escherichia coli* | CIP 54 127 |
| *Enterococcus hirae* | CIP 58.55 |
| Vancomycin-resistant *Enterococcus faecium*, vanA genotype | CIP 106 915 |
| Vancomycin-resistant *Enterococcus faecium*, vanB genotype | CIP 104 676 |

Count agar medium: casein tryptone soy agar.

Bouillon for the preparation of inocula: casein soy.

Protocol:

Deposit of 10 mL of supercooled agar in a Petri dish and solidified at ambient temperature.

Deposit of the cloth to be tested on agar:

Test cloth.

Normalized control cloth (neutral).

Test cloth+10% Dermal Betadine®.

Normalized control cloth+10% Dermal Betadine®.

Preparation of inocula containing 1 to $5×10^8$ CFU/mL for each strain tested.

Inoculation of 1 mL of inoculum in 150 mL of agar at 45° C.

Deposit of 5 mL of inoculated agar on the tested cloth, allowing to solidify.

Carrying out the tests in triplicate (test cloth and test cloth+10% Dermal Betadine®) and a simple test for the controls (normalized control cloth and normalized control cloth+10% Dermal Betadine®).

Incubation of the agars 24 hours at 37° C.

Verification of bacterial growth and determination of the width of the inhibition area, i.e. the area preserved from bacteria.

The evaluation of the bactericidal effect is based on the absence or presence of bacterial growth in the contact area between the agar and the tested cloth, and on the possible appearance of an inhibition area around the tested cloth.

ORC Cloth Results:

| Strains tested | Tested cloth | Inhibition area (mm) | Bacterial Growth | Evaluation of Bactericidal effect |
|---|---|---|---|---|
| Pseudomonas aeruginosa CIP 103 467 | Control cloth | 0 | Significant | Insufficient |
| | Control cloth + 10% Dermal Betadine ®. | 0 | Significant | Insufficient |
| | ORC cloth | 3 | non | Satisfactory |
| | ORC cloth + 10% Dermal Betadine ®. | 4 | non | Satisfactory |
| Staphylococcus aureus CIP 4.83 | Control cloth | 0 | Significant | Insufficient |
| | Control cloth + 10% Dermal Betadine ®. | 0 | Significant | Insufficient |
| | ORC cloth | 2.5 | non | Satisfactory |
| | ORC cloth + 10% Dermal Betadine ®. | 4.2 | non | Satisfactory |
| Escherichia coli CIP 54 127 | Control cloth | 0 | Significant | Insufficient |
| | Control cloth + 10% Dermal Betadine ®. | 0 | Significant | Insufficient |
| | ORC cloth | 0.6 | non | Satisfactory |
| | ORC cloth + 10% Dermal Betadine ®. | 2.3 | non | Satisfactory |
| Enterococcus hirae CIP 58.55 | Control cloth | 0 | Significant | Insufficient |
| | Control cloth + 10% Dermal Betadine ®. | 0 | Significant | Insufficient |
| | ORC cloth | 2 | non | Satisfactory |
| | ORC cloth + 10% Dermal Betadine ®. | 3.3 | non | Satisfactory |
| Methicillin Resistant Staphylococcus aureus CIP 103 811 | Control cloth | 0 | Significant | Insufficient |
| | Control cloth + 10% Dermal Betadine ®. | 0 | Significant | Insufficient |
| | ORC cloth | 2.2 | non | Satisfactory |
| | ORC cloth + 10% Dermal Betadine ®. | 3.6 | non | Satisfactory |
| Enterococcus faecium CIP 104 476 | Control cloth | 0 | Significant | Insufficient |
| | Control cloth + 10% Dermal Betadine ®. | 0 | Significant | Insufficient |
| | ORC cloth | 1.2 | non | Satisfactory |
| | ORC cloth + 10% Dermal Betadine ®. | 3.5 | non | Satisfactory |
| Enterococcus faecium CIP 106 915 | Control cloth | 0 | Significant | Insufficient |
| | Control cloth + 10% Dermal Betadine ®. | 0 | Significant | Insufficient |
| | ORC cloth | 1.7 | non | Satisfactory |
| | ORC cloth + 10% Dermal Betadine ®. | 5.5 | non | Satisfactory |

| Strains tested | Tested cloth | Inhibition area (mm) | Bacterial Growth | Evaluation of Bactericidal effect |
|---|---|---|---|---|
| Pseudomonas aeruginosa CIP 103 467 | Control cloth | 0 | Significant | Insufficient |
| | Control cloth + 10% Dermal Betadine ®. | 0 | Significant | Insufficient |
| | ONRC cloth | 0 | non | Satisfactory |
| | ONRC cloth + 10% Dermal Betadine ®. | 0.7 | non | Satisfactory |
| Staphylococcus aureus CIP 4.83 | Control cloth | 0 | Significant | Insufficient |
| | Control cloth + 10% Dermal Betadine ®. | 0 | Significant | Insufficient |
| | ONRC cloth | 0.5 | non | Satisfactory |
| | ONRC cloth + 10% Dermal Betadine ®. | 2.3 | non | Satisfactory |
| Escherichia coli CIP 54 127 | Control cloth | 0 | Significant | Insufficient |
| | Control cloth + 10% Dermal Betadine ®. | 0 | Significant | Insufficient |
| | ONRC cloth | 0 | non | Satisfactory |
| | ONRC cloth + 10% Dermal Betadine ®. | 1.7 | non | Satisfactory |
| Enterococcus hirae CIP 58.55 | Control cloth | 0 | Significant | Insufficient |
| | Control cloth + 10% Dermal Betadine ®. | 0 | Significant | Insufficient |
| | ONRC cloth | 1.5 | non | Satisfactory |
| | ONRC cloth + 10% Dermal Betadine ®. | 3 | non | Satisfactory |
| Methicillin Resistant Staphylococcus aureus CIP 103 811 | Control cloth | 0 | Significant | Insufficient |
| | Control cloth + 10% Dermal Betadine ®. | 0 | Significant | Insufficient |
| | ONRC cloth | 1 | non | Satisfactory |
| | ORC cloth + 10% Dermal Betadine ®. | 3.2 | non | Satisfactory |
| Enterococcus faecium CIP 104 476 | Control cloth | 0 | Significant | Insufficient |
| | Control cloth + 10% Dermal Betadine ®. | 0 | Significant | Insufficient |
| | ONRC cloth | 0.8 | non | Satisfactory |
| | ONRC cloth + 10% Dermal Betadine ®. | 3 | non | Satisfactory |

-continued

| Strains tested | Tested cloth | Inhibition area (mm) | Bacterial Growth | Evaluation of Bactericidal effect |
|---|---|---|---|---|
| Enterococcus faecium CIP 106 915 | Control cloth | 0 | Significant | Insufficient |
| | Control cloth + 10% Dermal Betadine ®. | 0 | Significant | Insufficient |
| | ONRC cloth | 2.2 | non | Satisfactory |
| | ONRC cloth + 10% Dermal Betadine ®. | 4 | non | Satisfactory |

CONCLUSION

The combination of oxidized regenerated or non-regenerated cellulose cloth, with 10% Dermal Betadine®, provides a bacterial inhibition superior to the mere use of oxidized cellulose cloth (regenerated or non-regenerated) alone or 10% Dermal Betadine® alone. These two constituents thus act in synergy.

We believe that it is the acidic pH of the hemostatic contact cloth that enhances the bactericidal effect of the povidone iodine.

Another aspect of the invention relates to a device for active protection of incision margins designed to prevent development of infections, comprising a surgical drape wherein a total or partial incision window is arranged, the borders of the aforementioned incision window incorporating an antibacterial agent in accordance with the invention.

This protection device is designed to be used in surgical operations in order to protect the incision margins. It is installed after the incision operation. The incision to be protected can also be an incision for trocar in the setting of laparoscopic surgery.

Referring to FIGS. 1a and 1b, the protective device in accordance with the invention comprises a surgical drape 1 provided with a partial or total incision window 2 through which the surgeon carries out his/her surgery.

The surgical drape 1 can be made in a single piece, but is optimally formed from a separable male part 1a and a separable female part 1b (FIG. 1a), the incision window 2 being arranged at the junction between the aforementioned male part 1a and the aforementioned female part 1b (FIG. 1b). The use of a surgical drape in two separable parts simplifies its design and its installation by the surgeon.

To adapt the size of the incision window 2 to the size of the incision to be made, the male part 1a and the female part 1b of the surgical drape 1 are maintained in position by an adjustable fastening device enabling adjustment of the position of the aforementioned male part with respect to the aforementioned female part and to vary the size of the aforementioned incision window.

Referring to FIGS. 1a and 1b, the adjustable fastening device is preferably formed by fastening lugs 1c arranged on the male part 1a and adapted to adhere to the female part 1b. The adhesive areas can possibly be protected by a removable protective paper that the operator will remove just before the installation. Any other equivalent adjustable fastening device can be used by the person of skill in the art, for example bands of loops and hooks (VELCRO®), or male elements inserted into female elements.

According to FIGS. 1a, 1b and 2, the female part 1b and the male part 1a are the male have straight borders, with incisions 1d on each side arranged so that the edges of the incision window 2 can be easily introduced into the surgical margin while maintaining the fixation lugs 1c outside the body of the patient. The incisions 1d are optimally configured so that approximately $\frac{4}{5}^{th}$ of the drape can be introduced into the surgical margin. According to an advantageous feature of the invention, the incisions 1d are precut so that the practitioner can introduce all or part of the borders of the incision window 2 into the surgical margin, at his/her discretion.

The surgical drape 1 comprises a base structure 3 made of a sterile nonwoven material of the cellulose wadding type, single layer or multi-layer. Any other material known to the person of skill in the art and suitable for the making of a surgical drape can be used. The base structure 3 has a width between 20 cm and 40 cm, a total length between 20 and 60 cm and a thickness ranging from 1 mm to 2 mm. However, these dimensions are not limiting and can be adapted by the person of skill in the art depending on the type of surgery performed.

In order to effectively isolate the body of the patient from the external environment, and particularly from the introduction of a contaminated fluid, the upper surface of a surgical drape 1 is waterproofed. This waterproofing can be made using a plastic film, a material impervious to liquids, a hydrophobic material or any other material suitable to the person of skill in the art.

In FIGS. 2 and 3, only the female part 1b of the surgical drape 1 is represented. However, the features shown also apply to the male part 1a or to the surgical drape 1 in the case where it is made in one piece.

In accordance with the invention and referring to FIGS. 1a and 1b, the internal face of the borders of the incision window 2 is covered by a means 4 for protecting the incision margins.

In accordance with the invention, this means of protection 4 comprises a layer 4b impregnated with an antiseptic-hemostatic and/or bactericidal and/or antibacterial and/or antibiotic and/or acidic ingredient.

According to an advantageous feature of the invention shown in FIG. 2 and enabling optimization of the protection of the incision margin, the means of protection 4 comprises a first layer 4a of a material designed to absorb the secretions from the incision and the second layer 4b impregnated with a antiseptic-hemostatic and/or bactericidal and/or antibacterial and/or antibiotic and/or acidic ingredient.

Referring to FIG. 4, the second layer 4b is arranged so that it contacts the incision margins 5 when setting up the surgical drape 1 around the incision. By "incision margins", it is meant that, in the meaning of the present invention, the cutaneous plane 5a and/or the subcutaneous plane 5b and/or the bone, muscular or fascial plane 5c.

According to an advantageous feature of the invention shown in the figures, the first layer 4a and the second layer 4b are arranged immediately adjacent to the borders of the incision window 2 to enable the surgeon to protect the incision margin 5 quickly by the simple crimping of the aforementioned edges in the body of the patient.

And in order to fully protect the incision margins 5, the second layer 4b is advantageously arranged so that comes into contact with the aforementioned margins and covers the top part and the bottom part of the incision during the installation of a spacer 6. Indeed, throughout the operation, the latter impacts and perfectly maintains the protective device object of the invention in position against the margins 5, without the edges of the incision window 2 interfering with the surgeon.

The first layer 4a can be of any conventional type. The absorbent materials commonly encountered are for example pulp, highly absorbent polymers, absorbent foam materials, and absorbent nonwoven fibers. It is possible to combine different materials in order to have different properties with respect to the liquid absorption capacity, distribution capacity and storage capacity. The material used is preferably, but not necessarily, a sterile thick absorbent compress of the HYDREX® type.

The second layer 4b is preferably made by a hemostatic contact cloth having an acidic pH combined with povidone iodine. Preferably used, as a hemostatic contact cloth, is regenerated (Surgicel®, Curacel®, Resorcel®, Promogran®, etc.) or non-regenerated (Gelitacel®, Curacel®, Okcel®) oxidized cellulose. In an implementation variation, the hemostatic contact cloth is oxidized cellulose, regenerated or non-regenerated, impregnated with chitosan (Chitoflex®, Chitoskin®, BST-Demon®, etc.). For the povidone iodine, known products such as, for example, Betadine®, Betaseptic®, Polydine®, Isodine®, Pevidine®, E-Z Scrub®, etc. can be used.

However, the second layer 4b can also be made by using a sterile compress of the HYDREX® type impregnated with an antiseptic-hemostatic and/or bactericidal and/or antibacterial and/or antibiotic and/or acidic ingredient. Any other equivalent material or coating adapted to be impregnated with such ingredients can be used by the person of skill in the art. This impregnation is for the purpose of preventing development of infections, parietes abscesses or hematomas. Among the utilizable impregnation ingredients, hemostatic ingredients, hydrogen peroxide, silver ion-based antiseptics, calcium alginate, Piliostigma Reticulatum, bacteriostatic agents, bactericidal agents, antibiotic molecules, acidic pH molecules, etc. can be cited as non-limiting example. These various impregnation ingredients can be used alone or in combination.

The second layer 4b totally or partially covers the first layer 4a. Referring to FIGS. 2 and 3, the first layer 4a is wider than the second layer 4b so that the first layer can effectively absorb and store bleeding or other bodily secretions. In practice, the first layer 4a has a length substantially equal to the width of the surgical drape 1 (and the male 1a and female 1b part), a width of approximately 10 cm and a thickness ranging from 4 mm to 6 mm. The second layer 4b also has a length substantially equal to the width of the surgical drape 1 (and the male 1a and female 1b part), a width of approximately 5 cm and a thickness ranging from 4 mm to 6 mm. However, these dimensions are not limiting and can be adapted by the person of skill in the art depending on the type of surgery performed.

Referring to FIGS. 2 to 4, the second layer 4b is advantageously coupled to an element 7 enabling impregnation, on demand, of the hemostatic contact cloth with povidone iodine.

This element 7 also enables impregnation of the sterile compress that can form the second layer 4b, with an antiseptic-hemostatic and/or bactericidal and/or antibacterial and/or antibiotic and/or acidic ingredient.

In practice, the second layer 4b is coupled to a tubing 7a connected to a member 7b enabling distribution, on demand, of povidone iodine (or any other active agent: a antiseptic-hemostatic and/or bactericidal and/or antibacterial and/or antibiotic and/or acidic agent), the aforementioned tubing comprising, in its distal part, perforations configured so that the povidone iodine (or any other active agent) can infuse the second layer.

The tubing 6a is advantageously placed between the second layer 4b and the base structure 3. It can possibly be embedded in the first layer 4a. This tubing 7a enables an irrigation of the second layer 4b, and therefore of the surgical incision site. This tubing 7a is perforated on a distal part, and on its proximal part; it is terminated by a connector of the Luer-lock® type connectable to a syringe or any other dispensing member 7b. In particular, in place of the syringe, a volumetric pump configured to irrigate the tube 7a, continuously and/or at the demand of the practitioner, can be used.

The instillation of an active ingredient (povidone iodine or other), can be carried out by this route, thus infusing the second layer 4b. These injections can be repeated over time, as the drape 1 is left in place.

The connection enabling the injection is preferably situated to the right of the male part 1a and to the left of the female part 1b, so that the two routes of injection are situated on the same side when the two parts are installed on each of the respective surgical incision margin 5. A Y-like double channel can be connected to these two injection sites in order to facilitate the instillations and in order to irrigate the two parts 1a and 1b by a single injection site.

In FIGS. 5 and 6, only the female part 1b of the surgical drape is shown. However, the features shown apply equally to the male part 1a or to the drape 1 in the case where it is made in single piece.

Referring to FIGS. 5 to 7, the internal face the borders of the incision window 2 can be coupled to an element 8 enabling the aspiration of secretions from the incision (bleeding and/or bodily secretions and/or free adipocyte magma and/or possible particles of glove talc, . . . ) at the incision margins 5. The practitioner thus has the option of draining the incision margin 5 and regularly evacuating secretions from the surgical site.

This feature must be understood as being independent of the design of the device object of the invention (a drape 1 made in a single piece or in two pieces) and in particular independent of the presence or not of the second layer 4b and of the antiseptic properties or not of the aforementioned device.

In practice, the first layer 4a designed to absorb the incision secretions is coupled to a tubing 8a connected to member 8b enabling aspiration of the aforementioned absorbed secretions and thus ensuring the drainage of the incision margins 5.

In the case where the first layer 4a is the thick sterile absorbent compress type, the tubing 8a is advantageously embedded in the aforementioned compress. If the first layer 4a is the type made from an absorbent foam material, the tubing 8a can be embedded in the aforementioned foam material or be placed against one of the faces of the aforementioned first layer, the vacuum created by the member 8b enabling aspiration of all the bleeding and/or absorbed bodily secretions.

The tubing 8a is advantageously perforated on a distal part and on its proximal part. It is terminated by a tip designed to be connected to the aspiration member 8b. In practice, a Luer-lock® type connector, connectable to a pump or any other aspiration member 8b, can be used. In practice, an electric pump housed in a portable housing or a vacuum wall outlet can be used. The aspiration can be performed continuously and/or at the demand of the practitioner.

The tubing 8a can be single or multiple. In the latter case, the tubing 8a has several branches arranged so as to homogenize the aspiration of incision secretions absorbed by the first layer 4a.

The connection enabling the aspiration is preferably situated to the right of the male portion 1a and to the left of the female portion 1b, so that the two suction channels are situated on the same side when the two parts are installed on each of the respective incision margins 5. A Y-like double channel can be connected to these two aspiration sites in order to be able to aspirate the incision secretions at the two parts 1a and 1b by a single aspiration site.

The tubing 8a enabling aspiration of the incision secretions absorbed by the first layer 4a can be the same tubing 7a enabling impregnation of the second layer 4b with an active ingredient. In an implementation variation, the tubings 7a and 8a are distinct.

The invention claimed is:

1. A device for active protection of incision margins designed to prevent development of infections, comprising a surgical drape wherein a total or partial incision window is arranged, the incision window defining borders, characterized by the fact that the borders of the incision window incorporate an antibacterial agent comprising as an active ingredient a hemostatic contact cloth having an acidic pH combined with povidone iodine.

2. A device according to claim 1, wherein:
an internal face of the borders of the incision window is covered by a first layer of a material designed to absorb secretions from the incision and a second layer impregnated with an antiseptic hemostatic ingredient designed to prevent the development of infections,
the second layer partially covers the first layer, the first layer being wider than the second layer,
the second layer is arranged so that it can come into contact with incision margins,
the second layer is an oxidized regenerated or non-regenerated cellulose cloth combined with povidone iodine.

3. A device according to claim 2, wherein the second layer is coupled to an element enabling impregnation, on demand, of the hemostatic contact cloth with povidone iodine.

4. A device according to claim 3, wherein the second layer is coupled to a tubing connected to a member enabling distribution, on demand, of povidone iodine, the tubing comprising, in its distal part, perforations configured so that the povidone iodine can infuse the second layer.

5. A device according to claim 1, wherein the borders of the incision window are arranged so that they can come into contact with the incision margins, an internal face of the edges of the window being covered by a layer of a material designed to absorb the secretions from the incision, the layer being coupled to a tubing connected to a member enabling aspiration of the absorbed secretions.

6. A device according to claim 5, wherein the layer designed to absorb the incision secretions is a thick, sterile, absorbent compress, the tubing being embedded in the compress.

7. A device according to claim 5, wherein the layer designed to absorb the incision secretions is an absorbent foam material, the tubing being embedded in the foam material.

8. A device according to claim 5, wherein the layer designed to absorb the incision secretions is an absorbent foam material, the tubing being placed against a face of the layer.

9. A device according to claim 5, wherein the tubing is perforated on a distal part, and on its proximal part; it is terminated by a nozzle designed to be connected to the aspiration member.

10. A device according to claim 5, wherein the tubing comprises several branches arranged so as to homogenize the aspiration of incision secretions absorbed by the layer.

* * * * *